United States Patent [19]

May et al.

[11] 4,159,333
[45] Jun. 26, 1979

[54] N-METHYL LEVO BENZOMORPHAN ANALGESICS HAVING NON-ADDICTIVE AND MORPHINE ANTAGONISTIC PROPERTIES

[75] Inventors: Everette L. May; Nathan B. Eddy, both of Bethesda, Md.

[73] Assignee: United States of America, Washington, D.C.

[21] Appl. No.: 940,863

[22] Filed: Sep. 8, 1978

Related U.S. Application Data

[63] Continuation of Ser. No. 45,553, Jun. 11, 1970, abandoned, which is a continuation-in-part of Ser. No. 801,209, Feb. 20, 1969, abandoned, which is a continuation-in-part of Ser. No. 643,382, Jun. 5, 1967, abandoned.

[51] Int. Cl.$^2$ ................... A61K 31/445; C07D 211/00
[52] U.S. Cl. ......................................... 424/267; 546/97
[58] Field of Search ................... 260/294.7 B; 424/267

[56] References Cited

U.S. PATENT DOCUMENTS

3,138,603   6/1924   May ...................................... 424/267

OTHER PUBLICATIONS

Archer et al., Journal of Medicinal Chemistry, vol. 7, No. 2, 3-6-64, p. 5.

Beckett et al., Journal of Pharmacy and Pharmacology, vol. 12, (1960), pp. 228T and 229T.
Chignell et al., Journal of Medicinal Chemistry, vol. 8, No. 2, (1965), pp. 235–237.
Fullerton et al., Journal of Organic Chemistry, vol. 27, No. 6, 1962, pp. 2144–2147.

*Primary Examiner*—Stanley J. Friedman
*Attorney, Agent, or Firm*—Holman & Stern

[57] ABSTRACT

Analgesic activity in man and animals is effected by administering an acid addition salt of the levo isomer of a compound of the structure

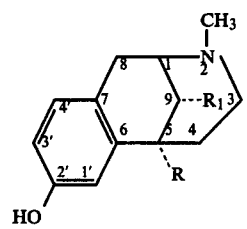

wherein R is a lower alkyl group and $R_1$ is a member of the group consisting of hydrogen and lower alkyl groups. Certain of the levo isomers are novel compounds.

26 Claims, No Drawings

N-METHYL LEVO BENZOMORPHAN ANALGESICS HAVING NON-ADDICTIVE AND MORPHINE ANTAGONISTIC PROPERTIES

This application is a continuation of application Ser. No. 45,553 filed June 11, 1970, which is a continuation-in-part of application Ser. No. 801,209 filed Feb. 20, 1969, now abandoned, which is a continuation-in-part of application Ser. No. 643,382 filed June 5, 1967, all are now abandoned.

This invention relates to novel analgesics and a method of effecting analgesic activity in man and animals by the administration of an acid addition salt of the levo isomer of a benzomorphan compound of the structure.

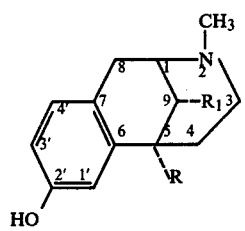

wherein R is a lower alkyl group and $R_1$ is a member of the group consisting of hydrogen and lower alkyl groups.

It is an object of this invention to provide novel analgesics and new analgesic methods employing active compounds of low toxicity, which are not habit-forming but exhibit morphine antagonism. Other objects and advantages will be apparent to those skilled in the art from the description herein.

The racemates of the above identified benzomorphan compounds are known to have analgesic properties.

The levo (−) isomers are twice as potent as the racemates, have no physical dependence capacity in monkeys but exhibit morphine antagonism whereas the racemates exhibit no such antagonism. The levo isomers are nalorphine-like.

The racemate, α-(+5,9 diethyl-2′-hydroxy-2-methyl-6,7-benzomorphan may be resolved into its optical isomers by means of d-mandelic acid (+)-3-bromo-8-camphorsulfonic acid, 1-mandelic acid or d-10-camphorsulfonic acid. Detailed procedures for resolution by these methods have been published by us in the Journal of Medicinal Chemistry, 9, 851–852 (1966) which is incorporated by reference in this application.

The racemates of the 5-methyl, the 5-ethyl and 5-propyl, 9-methyl compounds may be resolved by procedures set forth in detail herein.

The compounds are administered in the form of a water-soluble acid addition salts. Suitable salts include the hydrochloride, methyl sulfate, acetate, citrate, hydrobromide, nitrate, phosphate and tartrate, by way of example.

The compositions according to the present invention also comprise a pharmaceutical carrier which may be either a solid material or a liquid. Preparations for oral ingestion can be liquids or solids or any combination of these forms, such as syrups, elixirs, powders or tablets. Preparations for administration of the active agent in unit dose form can take the form of compressed powders or tablets or of a powder enclosed in a suitable capsule or absorbable material such as gelatin. The compressed powders or tablets may also comprise suitable excipients and/or diluents such as starch, lactose, stearic acid, magnesium stearate, dextrin or polyvinyl pyrrolidone.

Preparations for parenteral administration may be sterile solutions or suspensions in liquids such as water or physiological saline and may contain soluble or insoluble diluents and/or liquid excipients.

The unit dosage or therapeutically effective quantity of the analgetic agents of this invention may vary over wide limits; about 5 to 25mg./kg. of body weight for injectable compositions and about 20to 100mg./kg. of body weight for oral preparation.

The pain relieving capacity of the levo isomers of the invention are about equivalent to that of morphine but they possess no physical dependency liability in monkeys.

The pharmacological properties of the optical isomers are set forth in the following table:

| Compound[a] | ED$_{50}$[b] | PDC[c] | Antagonistic Activity[c] |
|---|---|---|---|
| (−) 5,9-dimethyl | 0.9 | No[d] | 1/50–1/30 Nalorphine |
| (+) 5,9-dimethyl | Inactive | No | No |
| (−) 5,9-diethyl | 1.2 | No[e] | 1/10 Nalorphine |
| (+) 5,9-diethyl | 7.9 | Intermediate | No |
| (−) 5-methyl | 1.8 | No[f] | 1/50 Nalorphine |
| (+) 5-methyl | 22.9 | Very low | No |
| (−) 5-ethyl | 0.6 | No[g] | 1/40–1/20 Nalorphine |
| (+) 5-ethyl | 21.8 | Low | No |
| (−) 5-propyl, 9-methyl | 0.8 | No[h] | 1/5 Nalorphine |
| (+) 5-propyl, 9-methyl | 12.3 | High | No |
| Morphine | 1.2 | High | No |
| Codeine | 7.5 | Intermediate | No |

[a]Administered as hydrochloride salts in water excepting morphine (as sulfate).
[b]Expressed in mg/kg (mice, subcutaneous administration); cf, N.B. Eddy and D. Leimbach, J. Pharmacol, Exptl. Therap., 107, 385 (1953) and A.E. Jacobson and E.L. May, J. Med. Chem., 8, 563 (1965).
[c]cf. Refs. 2, 3, and 4.
[d]From 0.5–8 mg/kg.
[e]From 0.5–32 mg/kg.
[f]From 1.0–20 mg/kg.
[g]From 2–16 mg/kg.
[h]From 0.5–2 mg/kg.

The following examples illustrate suitable therapeutic compositions:

EXAMPLE I

The following was prepared:

| | |
|---|---|
| α-(−)-5,9-diethyl-2'-hydroxy-2-methyl-6,7-benzomorphan hydrochloride | 15 g. |
| water | 1000 g. |

The water was distilled, pyrogen-free water. The solution was sealed in ampoules and sterilized after sealing for use for hypodermic injection.

EXAMPLE II

Tablets were prepared from the following (per tablet):

| | |
|---|---|
| α-(−)-5-propyl, 9-methyl-2'-hydroxy-2-methyl-6,7-benzomorphan hydrochloride | 250 mg. |
| lactose | 200 mg. |
| starch | 40 mg. |
| stearic acid | 5 mg. |
| sodium carboxymethyl cellulose | 0.2 mg. |

The CMC sodium salt was dispersed in water, the dispersion mixed with the remaining ingredients except stearic acid, the mixture passed through a 12 mesh standard sieve, dried, mixed with the stearic acid and compressed into tablets.

EXAMPLE III

Example I was repeated employing (−)-5-methyl-2'-hydroxy-2methyl-6,7-benzomorphan hydrochloride.

EXAMPLE IV (−)5-methyl-2'

Example I was repeated employing (−)-5-ethyl-2'hydroxy-2-methyl-6,7-benzomorphan hydrochloride.

EXAMPLE V

Example II was repeated employing α-(−)-5,9-diethyl-2'-hydroxy-2-methyl-6,7-benzomorphan acetate.

The following examples set forth the detailed resolutions of the racemates:

EXAMPLE VI

α-(±)-5-methyl-2'-hydroxy-2-methyl-6,7-benzomorphan

The racemate (2.2g), 1.8 g (1.15 equiv) of l-mandelic acid (Aldrich Chemical Company, Inc.), 10 ml of acetone and 1 ml of methanol were heated to solution and left at 25° for 3 hr and at −5° for 18 hr; yield 1.7 g, mp 175°-185°. This white solid, recrystallized from methanol gave 1.2 g of the (−)-l-mandelate, mp 190°-192°, which in methanol-aqueous ammonia yielded 0.65 g (60%) of l(-)free base; mp 211°−212°, $[\alpha]^{20}_D$ −72.5°, after a recrystallization from acetone or methanol. Anal. ($C_{14}H_{19}NO$) C, H; the Hydrochloride (from absolute ethanol-HCl then recrystallization from absolute ethanol), mp 262°−265°, $[\alpha]^{20}_D$ −49.6°. Anal. ($C_{14}H_{20}ClNO$) C, H.

The combined filtrates (from the 1.7 g of l-mandelate and from recrystallization of this 1.7 g) were concentrated to 2-3 ml and treated with excess aqueous ammonia to give 1.5 g of base mixture. This material, 1.2 g of d-mandelic acid (Aldrich), 6 ml of acetone and 2 ml of methanol were warmed to solution, cooled and kept at −5° for 1 hr to give 1.7 g of white solid, mp 184°-188°. One recrystallization from 5-6 ml of methanol gave 1.3 g of the (+)-d-mandelate, mp 191°-192.5° in turn converted to 0.7 g (63%) of the (+)-free base, mp 209°−210.5°, $[\alpha]^{20}_D$ +74.5°, after a recrystallization from acetone. Anal. ($C_{14}H_{19}NO$) C, H; the hydrochloride (from methanol-acetone) had mp 262°−265°, $[\alpha]^{20}_D$ +49.1°.

EXAMPLE VII

α-(±)-5ethyl-2'-hydroxy-2-methyl-6,7-benzomorphan

The racemate (5.0 g), 3.3 g of d-mandelic acid, 13 ml of absolute ethanol and 5 ml of acetone were heated to solution, filtered and left at 25° overnight to give 1.7 g (41%) of white solid which was recrystallized from methanol (4 ml) - acetone (15 ml). Cooling to 0° gave 0.9 g of the (−)-d-mandelate, mp 170.5°−172°, $[\alpha]^{20}_D$ +25.1). Anal. ($C_{23}H_{29}NO_4$) C, H. It gave 0.5 g of the (−) free base from aqueous ammonia; mp 208°-210° $[\alpha]^{20}_D$ −49.7°. Anal. ($C_{15}H_{21}NO$) C, H. The hygroscopic hydrochloride (from ethereal HCl) was recrystallized from methanol-acetone and carefully dried for 3 hr at 100° in vacuo just prior to analysis; mp 186.5°-188.5°, sealed capillary. Anal. ($C_{15}H_{22}ClNO$) C, H.

The combined filtrates (from isolation and recrystallization of the (−)-d-mandelate were concentrated to 7-10 ml, made basic with dilute ammonia diluted with $H_2O$, and cooled to give 4.3 g of a mixture of racemate and the d-isomer. This mixture, 2.8 g of l-mandelic acid, 8 ml of methanol and 35 ml of acetone were warmed to solution, filtered and the filter washed with acetone. The combined filtrate and washings were distilled to half volume, diluted with acetone and again distilled to half volume. Addition of acetone to 75 ml and refrigeration gave a white solid which was recrystallized from absolute ethanol (11 ml)-acetone (25 ml) giving 1.3 g (31%) of the (+)-l-mandelate, mp 170.5°-171.5°, $[\alpha]^{20}_D$ −21.3°. Anal. ($C_{23}H_{29}NO_4$) C, H. The (+) base melted at 209.5°−211.5° and had $[\alpha]^{24}_D$+51°. Anal. ($C_{15}H_{21}NO$) C, H. The hydrochloride had mp 188°-189° and was hygroscopic like the enantiomer. Anal. ($C_{15}H_{22}ClNO$) C, H.

EXAMPLE VIII

α-(±)-5-propyl-9-methyl-2'-hydroxy-2-methyl-6,7-benzomorphan

Absolute ethanol (20 ml), 2.0 g of racemate and 2.0 g of d-10-camphorsulfonic acid (Eastman) were heated to solution and left at room temperature for 6 hr to give 1.3 g of square plates, mp 245°-247° after filtration and washing with cold ethanol. This salt yielded 0.65 g (65%) of the (+) free base (from aqueous methanol-ammonia), mp 235°−237°, $[\alpha]^{20}_D$+69.8°, after a recrystallization from methanol. Anal. ($C_{17}H_{25}NO$) C, H, N. The hydrochloride (from isopropanol-diethyl ether) had mp 166°−169°, $[\alpha]^{20}_D$+50.8°. Anal. ($C_{17}H_{26}ClNO$) C, H, Cl.

The filtrate and washings from the 1.3 g of square plates above were made basic with ammonia and diluted with an equal volume of water. Cooling gave 1.2 g of the l-free base and racemate which, with 0.8 g of d-mandelic acid was heated to solution in 5ml of acetone. After 6 hr at 25° 1.1 g of the (−)-d-mandelate, mp 209°-211°, was filtered and converted to 0.65 (65%) of the (−) free base, mp. 236°−238°, $[\alpha]^{20}_D$−70.0, with methanol-dilute aqueous ammonia. Anal. ($C_{17}H_{25}NO$) C, H, N. The hydrochloride melted at 166°−169°; $[\alpha]^{20}_D$−49.3. Anal. ($C_{17}H_{26}ClNO$) C, H.

Analytical values were within ±0.3% of the theoretical values. Rotations in 95% ethanol (free bases and mandelate salts) and water (hydrochloride salts) were taken on a Perkin Elmer 141 Polarimeter, concentrations 1.0–1.4 g/100 ml of solution. Melting points (capillary) are corrected and expressed in °C.

REFERENCES (1) N. B. Eddy and E. L. May, "Synthetic Analgesics," Part II (B), 6,7-Benzomorphans," Pergamon Press, London, 1966, P 138 ff.

(2) G. A. Deneau, J. E. Villarreal, and M. H. Seevers, *Addendum* 2, Minutes of the 28th and 30th Meeting of the Committee on Problems of Drug Dependence, 1966, 1968, and J. E. Villarreal personal communication.

(3) J. E. Villarreal and M. H. Seevers, personal communication.

We claim:

1. A method of effecting analgesic and morphine antagonistic activity without producing physical dependence in animals which comprises administering to an animal an effective dosage of an acid addition salt of the levo isomer of a compound of the structure

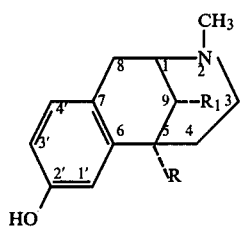

wherein R is a lower alkyl group and $R_1$ is hydrogen or a lower alkyl group, with the proviso that R and $R_1$ may not both be methyl.

2. The method of claim 1 wherein said compound is α-(−)-5,9-diethyl-2'-hydroxy-2-methyl-6,7-benzomorphan 3. The method of claim 1 wherein said compound is (−)-5-methyl-2'-hydroxy-2-methyl-6,7-benzomorphan.

4. The method of claim 1 wherein said compound is (−)-5-ethyl-2'-hydroxy-2-methyl-6,7-benzomorphan.

5. The method of claim 1 wherein said compound is α-(−)-5-propyl-9-methyl-2'-hydroxy-2-methyl-6,7-benzomorphan.

6. The method of claim 1 wherein said salt is the hydrochloride.

7. The method of claim 6 wherein said compound is α-(−)-5,9-diethyl-2'-hydroxy-2-methyl-6,7-benzomorphan.

8. The method of claim 6 wherein said compound is (−)-5-methyl-2'-hydroxy-2-methyl-6,7-benzomorphan.

9. The method of claim 6 wherein said compound is (−)-5-ethyl-2'- hydroxy-2-methyl-6,7-benzomorphan.

10. The method of claim 6 wherein said compound is α-(−)-5-propyl-9-methyl-2'-hydroxy-2-methyl-6,7-benzomorphan.

11. A pharmaceutical composition for internal administration having an analgesic, non-addictive, morphine-antagonistic effect which comprises a pharmaceutical carrier and an effective amount of an acid addition salt of α-(−)-5,9-diethyl-2-methyl hydroxy2-methyl-6,7-benzomorphan.

12. The composition of claim 11 wherein said salt is the hydrochloride.

13. The composition of claim 11 wherein said salt is the acetate.

14. A pharmaceutical composition for internal administration having an analgesic, non-addictive, morphineantagonistic effect which compises a pharmaceutical carrier and an effective amount of an acid addition salt of the levo isomer of a compound of the structure

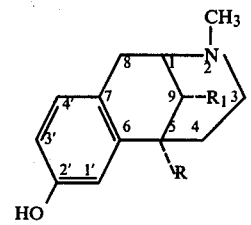

wherein R is a lower alkyl group and $R_1$ is hydrogen or a lower alkyl group, with the proviso that R and $R_1$ may not both be methyl.

15. The composition of claim 14, wherein said salt is the hydrochloride.

16. The composition of claim 14, wherein said salt is the acetate.

17. The composition of claim 14, wherein said compound is (−)-5-methyl-2'- -hydroxy-2-methyl-6,7-benzomorphan. methyl-6,7-benzomorphan.

18. The composition of claim 14, wherein said compound is (−)-5-ethyl-2'-hydroxy-2- methyl-6,7-benzomorphan.

19. The composition of claim 14, wherein said compound is α-(−)-5-propyl-9-methyl-2'-hydroxy-2-methyl-6,7-benzomorphan.

20. An acid addition salt of the levo isomer of a compound of the structure.

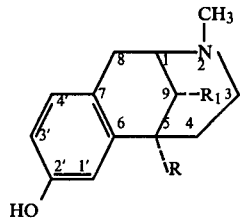

wherein R is a lower alkyl group and $R_1$ is hydrogen or a lower alkyl group, with the proviso that R and $R_1$ may not both be methyl.

21. The salt of claim 20, wherein said salt is the hydrochloride.

22. The salt of claim 20, wherein said salt is the acetate.

23. The salt of claim 20, wherein said compound is α-(−)-5,9-diethyl-2'-hydroxy-2-methyl-6,7-benzomorphan.

24. The salt of claim 20, wherein said compound is (−)-5-methyl-2'-hydroxy-2-methyl-6,7-benzomorphan.

25. The salt of claim 20, wherein said compound is (−)-5-ethyl-2'-hydroxy-2-methyl-6,7-benzomorphan.

26. The salt of claim 20, wherein said compound is α-(−)-5-propyl-9-methyl-2'-hydroxy-2-methyl-6,7-benzomorphan.

* * * * *